(12) United States Patent
Dusanter et al.

(10) Patent No.: US 10,278,638 B2
(45) Date of Patent: May 7, 2019

(54) SYSTEM AND METHOD TO MONITOR AND ASSIST INDIVIDUAL'S SLEEP

(71) Applicants: Florent Dusanter, Montrouge (FR); Ruiyi Yang, Coignieres (FR); Nadine Buard, Meudon (FR); Eric Carreel, Meudon (FR); Villard Joffrey, Paris (FR)

(72) Inventors: Florent Dusanter, Montrouge (FR); Ruiyi Yang, Coignieres (FR); Nadine Buard, Meudon (FR); Eric Carreel, Meudon (FR); Villard Joffrey, Paris (FR)

(73) Assignee: WITHINGS, Issy les Moulineaux (FR)

( * ) Notice: Subject to any disclaimer, the term of this patent is extended or adjusted under 35 U.S.C. 154(b) by 179 days.

(21) Appl. No.: 14/336,910

(22) Filed: Jul. 21, 2014

(65) Prior Publication Data

US 2016/0015314 A1    Jan. 21, 2016

(51) Int. Cl.
*A61B 5/00*        (2006.01)
*A61B 5/0205*    (2006.01)
(Continued)

(52) U.S. Cl.
CPC .......... *A61B 5/4812* (2013.01); *A61B 5/0024* (2013.01); *A61B 5/01* (2013.01); *A61B 5/02055* (2013.01); *A61B 5/02444* (2013.01); *A61B 5/0816* (2013.01); *A61B 5/1102* (2013.01); *A61B 5/113* (2013.01); *A61B 5/1126* (2013.01); *A61B 5/4815* (2013.01); *A61B 5/4818* (2013.01); *A61B 5/681* (2013.01); *A61B 5/6887* (2013.01); *A61B 5/6892* (2013.01);
(Continued)

(58) Field of Classification Search
CPC . A61B 5/4815; A61B 5/4818; A61B 10/0012; A61D 17/002
USPC .................................................. 600/300–301
See application file for complete search history.

(56) References Cited

U.S. PATENT DOCUMENTS 5,684,460 A * 11/1997 Scanlon ................. A61B 5/113
                                                                    340/573.1
6,599,251 B2 * 7/2003 Chen ...................... A61B 5/021
                                                                    600/481

(Continued)

FOREIGN PATENT DOCUMENTS

GB          2447640 A      9/2008
WO    WO 2007/052108 A2   5/2007
WO    WO 2007/052108 A3   5/2007

*Primary Examiner* — Christopher A Flory
*Assistant Examiner* — Shirley X Jian
(74) *Attorney, Agent, or Firm* — Miller, Matthias & Hull LLP

(57) ABSTRACT

A sleep assist system to monitor and assist the user's sleep, comprising: a bedside device adapted to be positioned near the user's bed, the bedside device optionally comprising a loudspeaker, a light source, a microphone, a light sensor, a temperature sensor, a control unit, an air quality sensor, a display unit, a user interface. The system further comprises a first sensing unit positioned in the user's bed comprising one or more sensors adapted to sense at least pressure and changes in pressure exerted by the user lying in the bed; an additional sensor device to be in contact with the user's body, and to be coupled to the bedside device; the system is configured to correlate the data obtained from both the first sensing unit and the additional sensor device.

10 Claims, 6 Drawing Sheets

(51) Int. Cl.

| | |
|---|---|
| *A61M 21/02* | (2006.01) |
| *A61B 5/08* | (2006.01) |
| *A61B 5/11* | (2006.01) |
| *A61B 10/00* | (2006.01) |
| *A61B 5/01* | (2006.01) |
| *A61B 5/024* | (2006.01) |
| *A61B 5/113* | (2006.01) |
| *A61M 16/16* | (2006.01) |
| *A61M 21/00* | (2006.01) |
| *A61B 5/029* | (2006.01) |
| *A61B 5/021* | (2006.01) |
| *A61B 5/145* | (2006.01) |
| *A61B 5/02* | (2006.01) |
| *A61B 5/026* | (2006.01) |
| *A61B 5/0285* | (2006.01) |
| *A61B 5/1455* | (2006.01) |
| *A61B 5/16* | (2006.01) |
| *A61F 5/56* | (2006.01) |
| *G01G 19/44* | (2006.01) |

(52) U.S. Cl.
CPC ............ *A61B 5/746* (2013.01); *A61B 5/7435* (2013.01); *A61B 10/0012* (2013.01); *A61M 16/161* (2014.02); *A61M 21/02* (2013.01); *A61B 5/0022* (2013.01); *A61B 5/021* (2013.01); *A61B 5/026* (2013.01); *A61B 5/02007* (2013.01); *A61B 5/029* (2013.01); *A61B 5/0285* (2013.01); *A61B 5/02125* (2013.01); *A61B 5/02405* (2013.01); *A61B 5/1118* (2013.01); *A61B 5/14542* (2013.01); *A61B 5/14551* (2013.01); *A61B 5/165* (2013.01); *A61B 5/4343* (2013.01); *A61B 5/747* (2013.01); *A61B 2010/0019* (2013.01); *A61B 2560/0242* (2013.01); *A61B 2562/0204* (2013.01); *A61B 2562/0247* (2013.01); *A61F 5/56* (2013.01); *A61M 2021/0027* (2013.01); *A61M 2021/0044* (2013.01); *A61M 2021/0083* (2013.01); *A61M 2205/3306* (2013.01); *A61M 2205/3368* (2013.01); *A61M 2230/06* (2013.01); *A61M 2230/205* (2013.01); *A61M 2230/30* (2013.01); *A61M 2230/63* (2013.01); *G01G 19/445* (2013.01)

(56) References Cited

U.S. PATENT DOCUMENTS

| | | | | | |
|---|---|---|---|---|---|
| 6,763,541 | B2* | 7/2004 | Mahoney | A47C 27/082 | 5/655.3 |
| 6,875,225 | B1* | 4/2005 | Pederson | A61M 21/00 | 607/88 |
| 7,214,196 | B2* | 5/2007 | Kodama | A61B 5/0537 | 600/551 |
| 7,248,915 | B2* | 7/2007 | Ronnholm | A61M 21/00 | 340/575 |
| 7,250,029 | B2* | 7/2007 | Fujita | A61B 5/18 | 600/300 |
| 7,396,331 | B2* | 7/2008 | Mack | A61B 5/024 | 600/300 |
| 7,572,225 | B2* | 8/2009 | Stahmann | A61B 5/00 | 600/300 |
| 7,654,948 | B2* | 2/2010 | Kaplan | A61B 5/4809 | 600/26 |
| 7,656,287 | B2* | 2/2010 | Albert | G06F 19/3418 | 340/521 |
| 7,850,720 | B2* | 12/2010 | Shefi | A61N 5/0613 | 607/88 |
| 8,211,014 | B2* | 7/2012 | David | A61B 5/7278 | 128/897 |
| 8,235,895 | B2* | 8/2012 | David | A61B 5/0205 | 128/897 |
| 8,348,840 | B2* | 1/2013 | Heit | A61M 21/00 | 600/300 |
| 8,469,884 | B2* | 6/2013 | David | A61B 5/7278 | 128/897 |
| 8,523,787 | B2* | 9/2013 | Ludwin | A61B 17/00234 | 600/437 |
| 8,603,010 | B2* | 12/2013 | Lange | A61B 5/113 | 600/584 |
| 8,781,568 | B2* | 7/2014 | Dugan | A61B 5/0002 | 600/519 |
| 8,979,731 | B2* | 3/2015 | Aarts | A61M 21/02 | 600/27 |
| 9,011,346 | B2* | 4/2015 | Wiard | A61B 5/02125 | 600/526 |
| 9,138,595 | B2* | 9/2015 | Savage | A61M 21/00 | |
| 9,241,637 | B2* | 1/2016 | Wiard | A61B 5/02125 | |
| 9,339,215 | B2* | 5/2016 | Van Vugt | A61B 5/113 | |
| 9,370,457 | B2* | 6/2016 | Nunn | A61G 7/015 | |
| 2002/0184711 | A1* | 12/2002 | Mahoney | A47C 27/082 | 5/713 |
| 2004/0249423 | A1* | 12/2004 | Savage | A61M 21/00 | 607/88 |
| 2005/0059870 | A1* | 3/2005 | Aceti | A61B 5/0002 | 600/340 |
| 2005/0061319 | A1* | 3/2005 | Hartley | A61B 5/0031 | 128/204.18 |
| 2005/0124864 | A1* | 6/2005 | Mack | A61B 5/024 | 600/300 |
| 2005/0190065 | A1* | 9/2005 | Ronnholm | A61M 21/00 | 340/575 |
| 2006/0009822 | A1* | 1/2006 | Savage | A61M 21/00 | 607/88 |
| 2006/0106437 | A1* | 5/2006 | Czeisler | A61M 21/02 | 607/88 |
| 2006/0241510 | A1* | 10/2006 | Halperin | A61B 5/113 | 600/534 |
| 2007/0118054 | A1* | 5/2007 | Pinhas | A61B 5/1102 | 600/587 |
| 2008/0269625 | A1* | 10/2008 | Halperin | A61B 5/113 | 600/508 |
| 2008/0275349 | A1* | 11/2008 | Halperin | A61B 5/0205 | 600/484 |
| 2009/0024004 | A1* | 1/2009 | Yang | A61B 5/0002 | 600/301 |
| 2009/0182189 | A1* | 7/2009 | Lira | A61M 21/00 | 600/27 |
| 2010/0094147 | A1* | 4/2010 | Inan | A61B 5/7207 | 600/500 |
| 2011/0046498 | A1* | 2/2011 | Klap | A61B 5/0205 | 600/534 |
| 2011/0112442 | A1* | 5/2011 | Meger | A61B 5/0002 | 600/595 |
| 2011/0137110 | A1* | 6/2011 | Aarts | A61M 21/02 | 600/27 |
| 2011/0190594 | A1* | 8/2011 | Heit | A61M 21/00 | 600/301 |
| 2011/0224510 | A1* | 9/2011 | Oakhill | G16H 50/30 | 600/301 |
| 2011/0263950 | A1* | 10/2011 | Larson | A61B 5/1113 | 128/845 |
| 2013/0141235 | A1* | 6/2013 | Utter, II | G08B 21/02 | 340/539.12 |
| 2013/0205501 | A1* | 8/2013 | Robertson | A61G 7/018 | 5/611 |
| 2013/0231582 | A1* | 9/2013 | Prasad | A61B 5/746 | 600/551 |
| 2013/0245502 | A1* | 9/2013 | Lange | A61B 5/1102 | 600/595 |
| 2013/0289770 | A1* | 10/2013 | Rawls-Meehan | G05B 15/02 | 700/275 |
| 2013/0310700 | A1* | 11/2013 | Wiard | A61B 5/02125 | 600/485 |
| 2014/0247136 | A1* | 9/2014 | Proud | G08C 17/02 | 340/870.01 |

(56) References Cited

U.S. PATENT DOCUMENTS

| | | | | |
|---|---|---|---|---|
| 2014/0259417 A1* | 9/2014 | Nunn | A61G 7/015 | 5/614 |
| 2015/0073283 A1* | 3/2015 | Van Vugt | A61B 5/113 | 600/476 |
| 2015/0112606 A1* | 4/2015 | He | A61B 5/0285 | 702/19 |
| 2015/0141852 A1* | 5/2015 | Dusanter | A61B 5/6892 | 600/484 |
| 2015/0164409 A1* | 6/2015 | Benson | G16H 50/30 | 600/301 |
| 2015/0173671 A1* | 6/2015 | Paalasmaa | A61B 5/0022 | 600/301 |
| 2015/0204561 A1* | 7/2015 | Sadwick | G05D 23/1905 | 236/1 C |
| 2015/0209597 A1* | 7/2015 | Haarlander | A61N 5/0618 | 601/46 |
| 2015/0282718 A1* | 10/2015 | Wiard | A61B 5/02125 | 600/483 |
| 2015/0320588 A1* | 11/2015 | Connor | A61F 7/0097 | 607/107 |
| 2015/0359452 A1* | 12/2015 | Giovangrandi | A61B 5/0295 | 600/547 |
| 2015/0359486 A1* | 12/2015 | Kovacs | A61B 5/0245 | 600/301 |
| 2016/0015314 A1* | 1/2016 | Dusanter | A61B 5/4812 | 600/301 |
| 2016/0015315 A1* | 1/2016 | Auphan | A61B 5/4815 | 600/301 |
| 2016/0058428 A1* | 3/2016 | Shinar | A61B 10/0012 | 600/301 |
| 2016/0058429 A1* | 3/2016 | Shinar | A61B 10/0012 | 600/551 |
| 2016/0095522 A1* | 4/2016 | Wiard | A61B 5/02125 | 600/483 |
| 2016/0174852 A1* | 6/2016 | He | A61B 5/7278 | 600/301 |
| 2016/0213354 A1* | 7/2016 | Levin | A61B 5/7275 | |
| 2016/0256080 A1* | 9/2016 | Shen | G06F 19/00 | |

\* cited by examiner

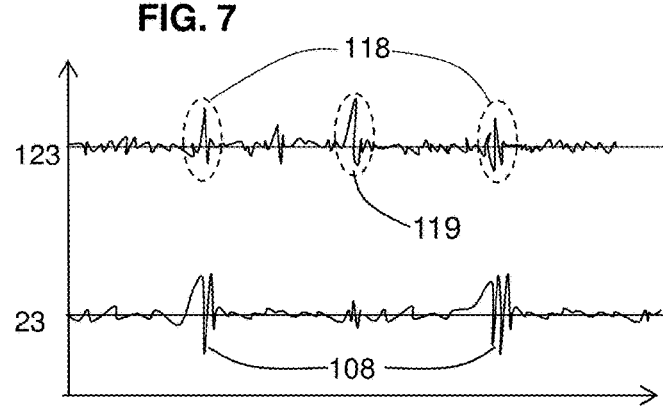
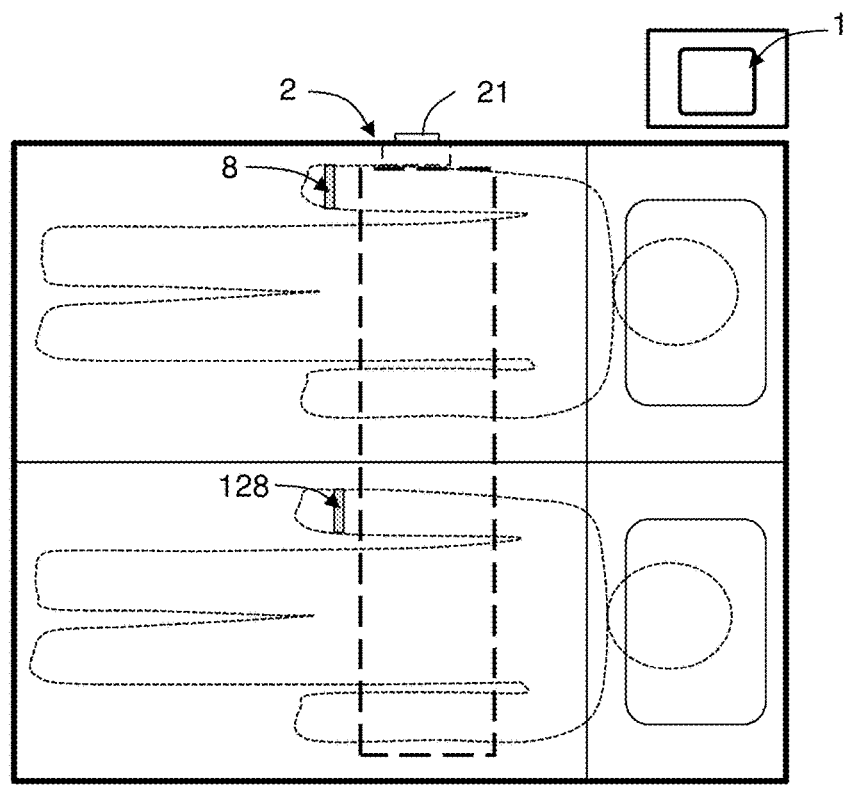

SYSTEM AND METHOD TO MONITOR AND ASSIST INDIVIDUAL'S SLEEP

FIELD OF THE DISCLOSURE

The present invention relates to systems and methods of monitoring and/or assisting individual's sleep.

BACKGROUND OF THE DISCLOSURE

More precisely, the present invention relates to a monitoring system, comprising a sleep sensing unit and a base unit. The sleep sensing unit is provided with sensor(s) (generally sensing functions), for example ballistography-based sensing functions. The base unit is coupled to the sleep sensing unit, and is configured to receive data measured by the sleep sensing unit and its own sensors. The base unit may inform the user of his/her sleep patterns, e.g. how often the user is awake during the night, or how many times the user enters the REM phase, and generally provide sleep stages and cycles timings like the one provided by PolySomnoGraphy systems.

Such systems as known in the art base the observations on the knowledge of what happens when the user is in a specific sleep stage. Generally, the average adult's sleep goes through sleep phases of REM sleep (paradoxical sleep) and NREM sleep; in average, there are 3-5 NREM/REM cycles, with average duration of 90-100 minutes. The NREM sleep is further divided into a light sleep and a deep sleep; in average, the deep sleep phases tend to be longer in $1^{st}$ part of the night, while the REM sleep tends to be longer in the $2^{nd}$ part of the night. For example in the light sleep, the user's breath is usually slower than when awake, and the heart rate is slowed down; in deep sleep, the heart rate and breathing frequency is further slowed, the muscles are relaxed and the movements are very little or non-existent; in REM phase, the heart rate and breathing frequency may increase again, and their variability is increased.

Some of the devices known in the art are configured to assist the user by providing other functionalities, such as a snooze alarm; some of the bedside devices may dim the lights when the user falls asleep, and put on the lights again once the user is awakened, or is to be awakened; some of the units serve mostly medical purposes, monitor the user's health, and are capable of issuing warning when the user's condition worsens.

Similar devices are known in the art. For example, GB2447640 describes a sensor wirelessly coupled to a base station. The sensor is head-worn and captures EEG of the user, while the base station processes the data and is capable of adjusting the user's sleep state. Another example is given in WO2007052108, which describes a system of sensors able to monitor medical conditions such as asthma, sleep apnea or labor, and notify medical personnel if needed. However, the system disclosed in WO200752108 does not provide the user with any means to adjust his/her sleep state.

Generally, the prior art systems are either too simple, thus not providing all the necessary information and not having all the required functionalities, or too complicated, thus being difficult to operate, prone to errors and failures, and providing the user with outputs that are confusing for him/her.

Therefore, there is a need to propose a user-friendly simple-to-use though elaborate sleep assist system.

SUMMARY OF THE INVENTION

A sleep assist system to monitor and assist the user's sleep is provided, the sleep assist system comprising: a bedside device adapted to be positioned near the user's bed, the bedside device further comprising at least one of the following: a loudspeaker, a light source, a microphone, a light sensor, a temperature sensor, a humidity sensor, a control unit, an air quality sensor, a display unit, a user interface; a first sensing unit adapted to be positioned in the user's bed, the first sensing unit comprising one or more sensors adapted to sense at least pressure and/or changes in pressure exerted by the user lying in the bed; an additional sensor device, adapted to be in contact with the user's body, and further adapted to be coupled to the bedside device; wherein the system is configured to correlate the data obtained from both the first sensing unit and the additional sensor device. The quality of the sleep of the user may thus be monitored and assessed based on various physiological parameters.

In the embodiments of the invention, one may use the sleep assist system as defined above, further having one or more of the following features:

the system is further configured to monitor the user's sleep, assess the user's sleep cycles and the phase of sleep cycle, and provide the user with at least one light and sound program, the light and sound program being based on the assessment of the user's sleep cycles and the phase of sleep cycle; the user may thus be assisted in improvement of the sleep quality;

the system is configured to monitor the user's sleep, assess the user's sleep cycles and the phase of sleep cycle; the additional sensor device is adapted to measure the user's heart rate level and variability and/or the respiration rate level and variability and/or the user's skin temperature; and the system is further configured to assess a current phase of the female menstrual cycle based on an analysis of heart rate level and variability and/or the respiration rate level and variablilty and/or the skin temperature during deep sleep phase; the female user is thus informed about her menstrual cycle;

the system is configured to monitor the user's sleep, assess the user's sleep cycles and the phase of sleep cycle, the additional sensor device is adapted to measure the user's heart pulse (e.g. PhotoPlethysmoGraphy sensor), the first sensing unit is adapted to measure balistography signal, namely BCG, and the system is further configured to assess the stiffness of the user's arteries based on the measurements of the Pulse transit Time between the BCG signal measured by the first sensing unit and the PPG signal measured by the additional sensor device; ; the health risk for the user may thus be evaluated and the user may be informed about the state of his/her arteries;

the system is configured to monitor the user's sleep, assess the user's sleep cycles and the phase of sleep cycle, the first sensing unit is adapted to measure balistography signal, and the system is further configured to assess the heart volume stroke or at least its evolutions based on the measurements of the amplitude of the BCG signal measured by the sensing unit; the health risk for the user may thus be evaluated and the user may be informed about the state of his heart;

the system is configured to monitor the user's sleep, assess the user's sleep cycles and the phase of sleep cycle, the additional sensor device is adapted to measure the user's heart pulse (e.g. PhotoPlethysmoGraphy sensor), the sensing unit is adapted to measure balistography signal, and the system is further configured to assess the blood pressure or at least its evolutions based on the combination of the measurements of arterial stiffness, volume stroke and heart rate; the health risk for the user may thus be evaluated and the user may be informed about the state of his/her cardiovascular system;

the bedside device and/or the sensing unit are adapted to detect user's breathing and/or snoring, and/or the additional sensor device is adapted to detect blood oxygenation, and wherein the sleep assist system is configured to assess whether the user suffers from sleep apnea; the user is then informed about the state and may thus seek appropriate medical assistance;

the system is further adapted provide an alert to third person in the case when the system is used by people with medical condition, elderly people and/or pregnant women and an unexpected situation occurs; the third persons such as medical personnel, relatives or carers are thus informed about the unexpected situation and/or possible health risks;

the system further comprises a scale, and wherein the system is configured to correlate the data obtained from the first sensing unit, the additional sensor device, and a scale; the user may thus be informed about his physical state and quality of sleep more comprehensively;

the additional sensor device further serves as a physical activity monitor, and is adapted to measure parameters related to the physical activity; the user may thus be informed about his physical state and quality of sleep more comprehensively.

the system further comprises a mobile terminal, the mobile terminal is configured to display the information obtained by the bedside unit, the sensing unit and/or the additional sensor device; the user may thus conveniently obtain information on his/her sleep cycles and overall state;

the mobile terminal is further configured to receive feedback from the user and adjust the sleep assist system accordingly; the user may thus influence the sleep assist system.

In an alternative embodiment, a sleep assist system to monitor and assist the user's sleep is provided, the sleep assist system comprising: a bedside device adapted to be positioned near the user's bed, the bedside device comprising a loudspeaker, a light source, a microphone and a light sensor; a first sensing unit adapted to be positioned in the user's bed, the first sensing unit comprising one or more sensors adapted to sense pressure and/or changes in pressure exerted by the user lying in the bed; a mobile terminal, configured to be connected at least to the bedside device; an additional sensor device, adapted to be in contact with the user's body, and further adapted to be coupled to the bedside device; wherein the system is configured to: monitor the user's sleep, assess the user's sleep cycles and the phase of sleep cycle, using the first sensing unit and the additional sensor device, monitor the user's environment, using the bedside device, provide feedback to the user through the mobile terminal, and provide the user with at least one light and sound program, the light and sound program being based on the assessment of the user's sleep cycles and the phase of sleep cycle.

In a further alternative embodiment, a sleep assist system to monitor and assist the user's sleep is provided, the sleep assist system comprising: a bedside device adapted to be positioned near the user's bed, the bedside device comprising a control unit and a user interface; a first sensing unit adapted to be positioned in the user's bed, the first sensing unit comprising one or more sensors adapted to sense at least pressure and/or changes in pressure exerted by the user lying in the bed and coupled to the bedside device; wherein the system is adapted to measure the variations of the user's weight over a substantive period of time. To do so, the period in the night where the largest pressures are seen during a sufficient time are averaged. This alternative embodiment may readily be combined with the features of the embodiments described above.

In a further alternative embodiment, a sleep assist system to monitor and assist the user's sleep is provided, the sleep assist system comprising: a first sensing unit adapted to be positioned in the user's bed, the first sensing unit comprising one or more sensors adapted to sense at least pressure and/or changes in pressure exerted by the user lying in the bed; a mobile terminal coupled to the a first sensing unit, wherein the system is adapted to measure the variations of the user's weight over substantive period of time. To do so, the period in the night where the largest pressures are seen during a sufficient time are averaged.

For example, the alternative embodiment may use one or more of the following features:

the system is further adapted to measure the user's heart rate and/or breathing frequency, and, based on the data, to assess the to assess the female menstrual cycle based on an analysis of user's body weight, heart rate and/or skin temperature; the user is thus informed about her cycle;

the system is further configured to alarm the medical personnel when appropriate.

In a further alternative embodiment, a sleep assist system to monitor and assist the user's sleep is provided, the sleep assist system comprising: a first sensing unit adapted to be positioned in the user's bed, the first sensing unit comprising one or more sensors adapted to sense at least pressure and/or changes in pressure exerted by the user lying in the bed; an additional sensor device, adapted to be in contact with the user's body, and further adapted to be coupled to the bedside device; a mobile terminal coupled directly to the a first sensing unit and additional sensor device; wherein the system is configured to correlate the data obtained from both the first sensing unit and the additional sensor device.

The system from this alternative embodiment may be readily combined with the features of the embodiments described above; for instance, one may use one or more of the following:

the system is configured to monitor the user's sleep, assess the user's sleep cycles and the phase of sleep cycle, wherein the sensing unit is adapted to measure the user's heart rate level and/or heart rate variability and/or respiration rate and/or respiration rate variability, and wherein the system is further configured to assess a current phase of the female menstrual cycle based on a monthly periodic analysis of heart rate level and heart rate variability level variation in deep sleep phase, and/or temperature during deep sleep phase; the female user is thus informed about her menstrual cycle the mobile terminal together with the sensing unit and/or the additional device are adapted to detect user's breathing and/or snoring, and wherein the sleep assist system is configured to assess whether the user suffers from sleep apnea by detecting respiration stops and/or blood oxygenation drops; the user is then informed about the state and may thus seek appropriate medical assistance.

the system is configured to monitor the user's sleep, the additional sensor device is adapted to measure the user's heart pulse (e.g. PhotoPlethysmoGraphy sensor), the first sensing unit is adapted to measure balistography signal, namely BCG, and the system is further configured to assess the stiffness of the user's arteries based on the measurements of the Pulse transit Time between the BCG signal measured by the first sensing unit and the PPG signal measured by the additional sensor device; the health risk for the user may thus be evaluated and the user may be informed about the state of his/her arteries;

the system is configured to monitor the user's sleep, assess the user's sleep cycles and the phase of sleep cycle, the first sensing unit is adapted to measure balistography signal, and the system is further configured to assess the heart volume stroke or at least its evolutions based on the measurements of the amplitude of the BCG signal measured by the sensing unit; the health risk for the user may thus be evaluated and the user may be informed about the state of his heart;

the system is configured to monitor the user's sleep, assess the user's sleep cycles and the phase of sleep cycle, the additional sensor device is adapted to measure the user's heart pulse (e.g. PhotoPlethysmoGraphy sensor), the sensing unit is adapted to measure balistography signal, and the system is further configured to assess the blood pressure or at least its evolutions based on the combination of the measurements of arterial stiffness, volume stroke and heart rate; the health risk for the user may thus be evaluated and the user may be informed about the state of his/her cardiovascular system.

The sleep assist system of the present invention is designed to both monitor and improve the sleep quality. To this end, the present invention provide a simple yet comprehensive system of a sensing unit, a bedside device, and a mobile terminal, which together may help monitor the sleep cycles and/or improve the user's sleep.

One of the aims of the present invention is to provide the user with improved understanding of individual sleep patterns and information on how the environment affects sleep quality. The user can visualize his/her sleeping patterns, understand what wakes him/her up and compare past nights. He can also correlate with the activity done, the meals and drinks taken the day before. The present invention lets the user set personalized sleep and wake-up programs including the wake-up time schedule.

The sleep assist system according to the present invention records & analyzes sleep environment information to understand what can have a positive or negative impact on sleep quality; correlates sleep data and sleep environment data to detect what elements of the environment can have impacted sleep quality; and allows the user to visualize his/her sleep stage recordings and get insights into what elements of the environment can have impacted sleep quality.

In particular, the embodiments of the invention may help to assess the impact of the following influences on sleep cycles, sleep quality and wake-up quality:

the sound levels and sound events
the temperature and humidity levels and variations
the light levels and variations
the weather
the atmospheric pressure
the moon cycles
the air quality
the food and/or drink intake
the jet-lag, etc . . . .

In an embodiment, the sleep assist system provides a mobile terminal with an application which may connect wirelessly or through a wire to the bedside device or to the sensing unit, and allows the user to access all his/her collected data. The user can visualize his/her sleeping patterns, understand what wakes him/her up and compare past nights. The application lets the user set all personalized sleep and wake-up programs including the wake-up time schedule. Based on the user settings and preferences, the sleep assist system will do some real-time adjustment and start its progressive wake-up program at the most beneficial time of the sleep cycle which is considered to be the light sleep stage.

BRIEF DESCRIPTION OF THE DRAWINGS

Other characteristics and advantages of the invention will readily appear from the following description of one of its embodiments, provided as a non-limitative examples, and of the accompanying drawings.

FIG. 7 shows an illustrative time chart relative to the system of FIG. 6

FIG. 8 is analogous to FIG. 5, with further sensor devices used

DETAILED DESCRIPTION

Figure 1A:
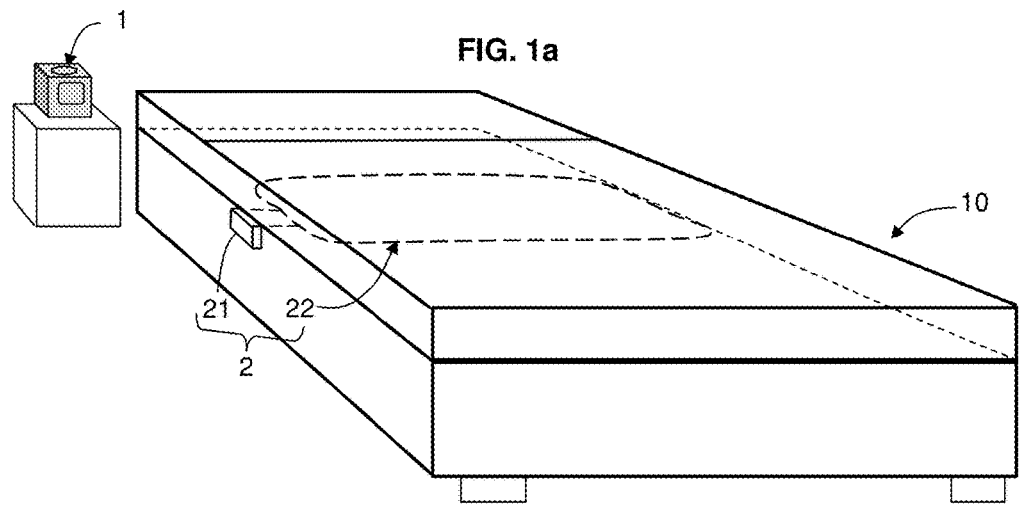
FIGS. 1a and 1b are schematic views of a bed with the sleep sensing unit and the bedside device
Figure 1B:
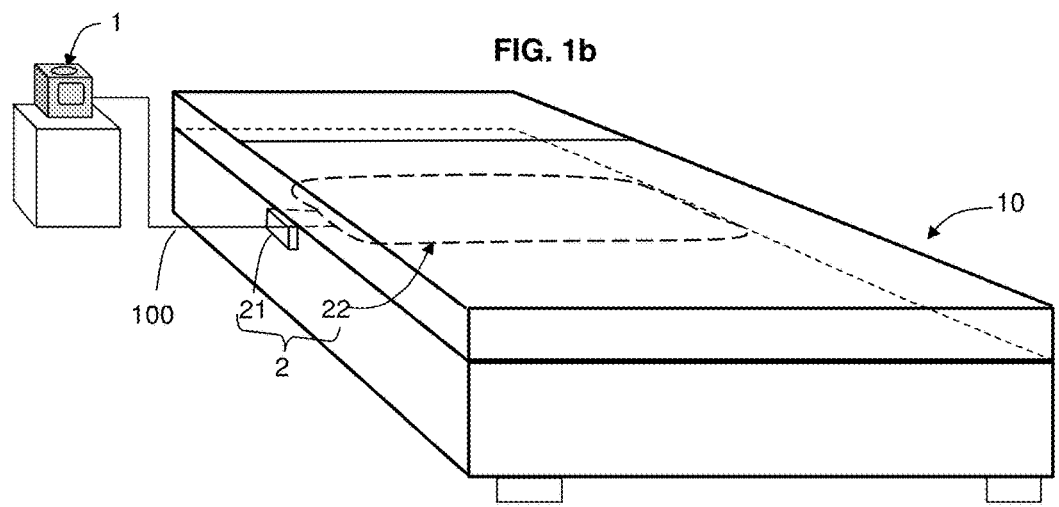

FIGS. 1a, 1b, 2, 4, 5, 6 and 8 show an example of the sleep assist system according to the present invention. The sleep assist system comprises a bedside device 1 and a sleep sensing unit 2, also called 'first sensing unit' in some parts of the present document.

The bedside device 1 may be positioned such that the user has an easy access to the bedside device 1, e.g. on a bedside table, a stand or the like. The sleep sensing unit 2 may be positioned in or near the user's bed; preferably, the bedside device 1 is positioned in proximity to user's bed.

It should be noted that the proposed system is a home appliance, intended to be used mainly at home by one or more individual(s), and is not intended to be used by physicians or doctors in hospitals or the like.

The sleep sensing unit 2 is coupled to the bedside device 1. In one embodiment, the connection is wireless. Such wireless connection may use for example a Wifi connection, Bluetooth, or any energy saving short range wireless link. Alternatively, the bedside device 1 and the sleep sensing unit 2 may be connected via a wire 100, for example through a USB/micro-USB cable connection. The bedside device 1 and the sleep sensing unit 2 may also provide both possibilities for the user to choose.

In the embodiment shown on FIG. 1, the sleep sensing unit 2 comprises an electronic unit 21 and a sensing portion 22. The sensing portion 22 is configured to measure one or several parameters, such as the user's heart rate, user's position and/or movements, breathing frequency, skin temperature, body weight etc. To this end, the sensing portion 22 may be equipped with sensors to sense the changes of the pressure generated by the user's body; temperature sensors to sense user's skin temperature; etc. For example, the sensors to sense the pressure changes may be piezoelectric sensors, piezoresistive sensors, or the like.

In a preferred embodiment, the sensing unit 2 is switched on/off automatically, without the need for the user to perform any action but lie down/go up. The sensing unit 2 starts to gather data as soon as the user is present in the bed and stops as soon as the user leaves the bed.

Preferably, the data recorded by the sensing unit 2 is recorded in real time.

In one embodiment, the sleep sensing unit 2 may further be pneumatic, i.e. comprising an air bladder which is adapted to be filled with air at specific moments. Possibly, the air-filling and release of air may be periodically repeated so as to generate pulses. The timing and intensity of the pulses is preferably controlled by the bedside device 1. Alternatively, it may be controlled by the electronic unit 21.

The data obtained from the sleep sensing unit 2 may be subsequently transmitted to the bedside device 1 via the electronic unit 21. The data can be sent to the bedside device 1 in real time or be first processed in the sensor unit 2. Alternatively, the data may be sent in batches.

Alternatively, the data may be transmitted to a mobile terminal 7 (described below) instead of the bedside device 1, or may be transmitted to both mobile terminal 7 and the bedside device 1. To this end, the electronic unit 21 may comprise a communication interface 23 (shown on FIGS. 2 and 4). In the embodiment shown on FIG. 1, the sensing portion 22 is provided in the form of a pad. The pad may be positioned under the mattress 10, on which the user sleeps; alternatively, it may be positioned under a mattress topper, under a bed sheet, or on the top of a bed sheet so that the user is in direct contact with the pad. Preferably, the pad is positioned at least under the chest area of the user. In an alternative embodiment, the sensing portion 22 may be provided as a device which is in direct contact with the user's body, for example on user's wrist, head, chest, etc. As a further alternative, the pad form of the sensing portion 22 and the device in direct contact with the user's body may be combined, i.e. there may be two or more sensing portions 22.

Figure 2:
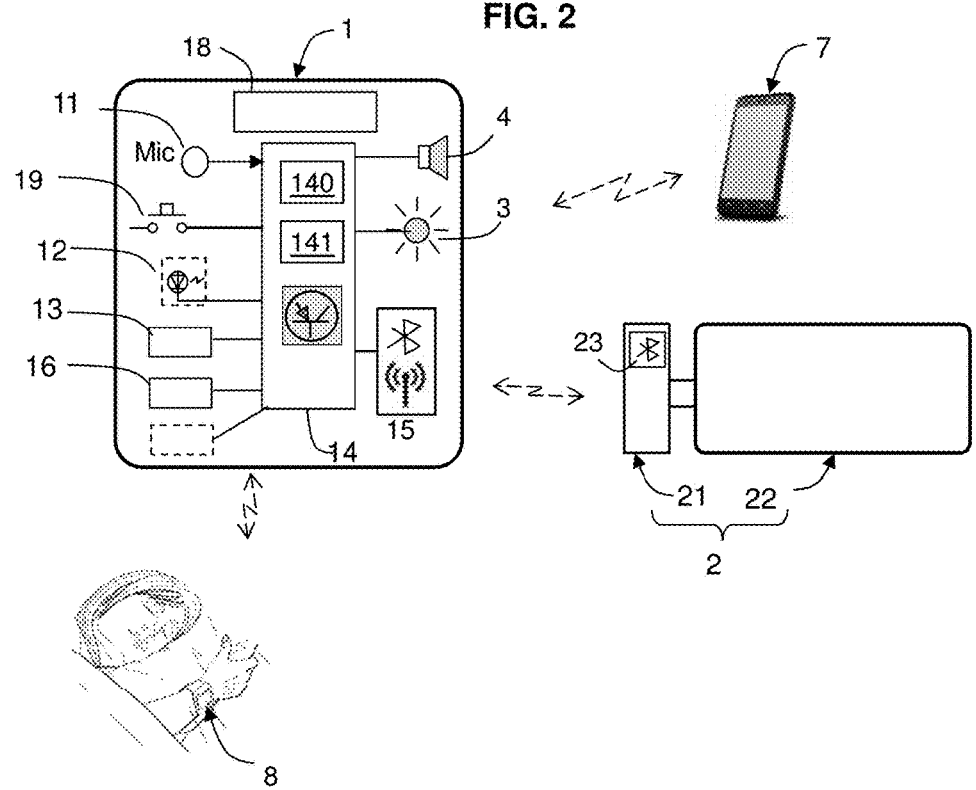
FIG. 2 is schematic functional block diagrams of the bedside device, as well as the devices coupled to the bedside device
Figure 4:
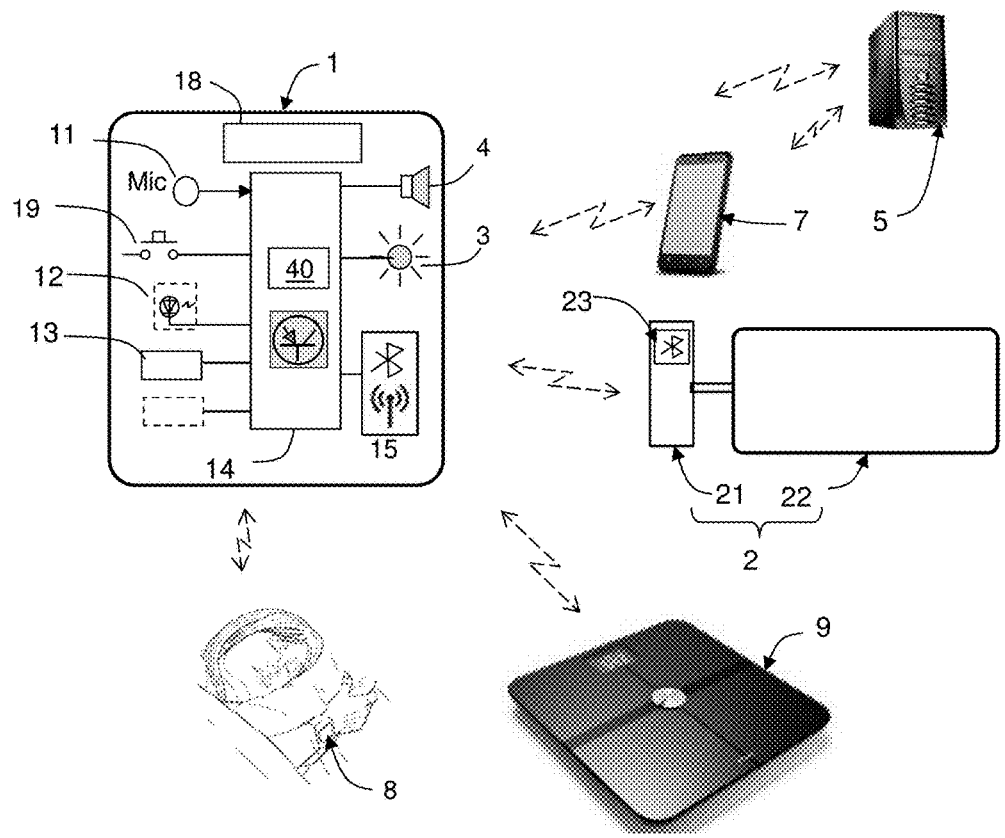
FIG. 4 is analogous to FIG. 2; it shows the system in an enlarged perimeter.

FIGS. 2 and 4 show a schematic drawing of the sleep assist system. The system comprises the bedside device 1 and the sleep sensing unit 2. The bedside device 1 comprises a communication interface 15. For example, the communication interface 15 is configured to communicate wirelessly with one or more devices (described below). The one or more devices may be each configured to communicate with the bedside device 1 e.g. via BlueTooth™, Wifi, or other suitable wireless means. Alternatively, the communication may be wired.

The sleep assist system may further comprise a mobile terminal 7, such as a cell phone. Alternatively, the mobile terminal may be replaced or complemented by a computer, a laptop, a tablet or the like. Below, an example with the mobile terminal 7 is described; however, it is to be understood that all the functions described below for the mobile terminal 7 may be performed by any supplementary or replacement device such as the computer, the laptop, the tablet or the like.

The mobile terminal 7 communicates with the bedside device 1 and may be used for controlling and/or programming the bedside device 1. To this aim, the mobile terminal 7 may be equipped with a specialised application (alternatively, a specialised computer program), which enables the user to control the bedside device 1 and to set the requested parameters. The mobile terminal 7 and/or the other devices used are preferably connected to the internet. The specialised application may be for example downloaded from the Internet. Further functions of the mobile terminal 7 will be described later.

The sleep assist system may further comprise any additional sensor device 8, such as a wrist-worn device 8. Alternatively, the additional sensor device 8 may be worn on user's head, chest, leg, etc. It may comprise one or several additional sensors, used to assess the user's skin temperature, heart rate, etc. The additional sensor device 8 may be a multi-purpose sensor device, which may be used not only while sleeping, but also for example while working out, jogging etc. To this end, the additional sensor device 8 may be equipped with further related functions. The sensor device 8 is preferably configured to wirelessly transmit the obtained data to the bedside device 1 and/or the mobile terminal 7.

The sleep assist system may further comprise a scale 9; example of such system is given on FIG. 4. The scale 9 is adapted to provide additional information to the system about the user's health. The scale 9 may for example be adapted to measure user's weight, the percentage of bodily fat, etc. Optionally, the scale 9 may also record and/or transmit to the mobile terminal 7 the changes of the measured parameters. The scale 9 is preferably adapted to transmit the obtained data to the bedside device 1 and/or the mobile terminal 7, either wirelessly or via a wired link.

In one embodiment, the sleep assist system may further comprise a remote server 5 (may be seen on FIG. 4). The remote server 5 is preferably connected to the internet, and communicates via the internet with the mobile terminal 7, the bedside device 1, and/or the sensing unit 2, and/or the additional sensor device 8. The remote server 5 is configured to receive the sensory data. In one embodiment, the remote server may be connected to a plurality of sleep assist systems, which may all transmit their respective sensory data to the remote server 5. The remote server 5 may then analyse both individual data (i.e. data obtained by a single sleep assist system) and collective data (i.e. data obtained by group of sleep assist systems).

The information thus obtained by the remote server 5 may be used in a statistic analysis of the influence of geographical position, weather, age, health/fitness, weight of the user etc. on the quality of the users' sleep. The data and the statistical analysis may be further used for example to detect potential prevalence or risk of short-term illness (e.g. flu, cold, laryngitis) and/or chronic diseases (e.g. heart conditions, Parkinson disease).

The data and statistical analysis may be then transmitted back to the respective bedside device 1 and/or the respective mobile terminal 7, and displayed to the user.

Some or all of the components of the sleep assist system may be coupled to the bedside device 1. Preferably, at least some of the components are connected wirelessly to the bedside device 1, directly or indirectly. Some or all of the components of the sleep assist system may also be interconnected with each other, either wirelessly or via wires. For example, the additional sensor device 8 may be connected directly to the mobile terminal 7, or may be connected to the bedside device 1, which is in turn connected to the mobile terminal 7.

The bedside device 1 may also be equipped with one or more USB/micro USB ports to allow the user to import/export data easily either via wired connection, or via a USB stick.

The bedside device 1 may further comprise one or more of the following components: a microphone 11, a light sensor 12, a temperature sensor 13, a control unit 14, an air quality sensor 16, a humidity sensor, a display unit 18, a user interface 19 (for example a touch interface/a movement sensor configured to recognize touches, gestures, and the like), a light source 3, a loudspeaker 4.

The microphone 11, the light sensor 12, the temperature sensor 13 and the air quality sensor 16 provided on the bedside device 1 may be of any type known in the art.

The microphone 11 is adapted to detect and record sounds that surround the user, for example noises from the street, user's breathing, snoring (of either the user, or the user's partner who is sleeping in the same room), etc.

The light sensor 12 is adapted to detect the light that surrounds the user, such as daylight, or artificial light, coming either from the inside (e.g. the house lights), or outside (e.g. street lamps, cars passing by).

The temperature sensor 13 is adapted to detect the ambient temperature of the room. The air quality sensor 16 may be further divided into carbon dioxide concentration sensor, Volatile Organic Compound (VOC) sensor, other gas or dust sensor, air humidity sensor, and the like; it is adapted to measure and assess the quality of the air in the room.

The microphone 11, the light sensor 12, the temperature sensor 13 and the air quality sensor 16 are all connected to the control unit 14. The control unit 14 is equipped with a processing unit 140 and a memory unit 141, and is capable of processing the data obtained from the sensors. Preferably, the processing unit 140 is configured to assess the user's sleep cycles based on the data obtained from the sensors.

The light source 3 provided on the bedside device 1 is preferably adapted to emit light of several different colors (e.g. white, red, orange, yellow, green, turquoise, blue, violet; other colors not being excluded). Preferably, the light emitted by the light source 3 may also be of variable intensity. In other words, the light source 3 is able to emit multi-wavelength/multi-color LED lighting programs or static lights. For example, the light source 3 may use a multi-color LED dimming lighting technology.

The loudspeaker 4 may be of any type known in the art. The loudspeaker 4 may be provided directly in the bedside device itself. Alternatively, it may be provided separately, as a bedside-device-driven sound system. The loudspeaker 4 is preferably able to diffuse sounds of frequencies within the audible range.

The light source 3 and the loudspeaker 4 are connected to the control unit 14. The control unit 14 controls the loudspeaker 4 and/or the light source 3, based on the inputs from the sensing portion 21 of the sensing unit 2, as well as from the microphone 11, the light sensor 12, the temperature sensor 13 and the additional sensor device 8, if provided.

The bedside device 1 may further be provided with a display unit 18. The display unit may display various kinds of information, such as time, ambient temperature, level of noise, etc. In the displayed information, the sensory data (such as user's heart rate) obtained from the above-described sensors may be displayed.

The bedside device 1 may further be provided with a user interface 19. The user interface 19 may be in the form of physical buttons. Preferably, the user interface comprises touch areas (one or more touch screens) and/or movement sensors. The touch areas and/or movement sensors may be adapted to recognize various predefined or pre-set touches and/or movements, through which the user may communicate with the bedside device 1. For example, movements may be predefined or pre-set to set the alarm, switch on/off the lights, adjust the light intensity and sound volume, start/stop the light and sound programs (described below), snooze wake program, switch off the bedside device 1 completely, etc. Further, some or all of the touches/gestures may be adjusted by the user to suit him/her best.

The memory unit 141 stores data obtained from the sensing portion 21 of the sensing unit 2, as well as from the microphone 11, the light sensor 12, the temperature sensor 13, the air quality sensor 16, the additional sensor device 8, etc. In one embodiment, the processing unit 140 of the bedside device 1 is configured to analyse the user's sleep cycles, based on the data obtained from the sensing unit 2 and possibly also the additional sensor device 8. The sensing unit 2 and/or the additional sensor device 8 provide data about the user's heart rate and variability, breathing frequency and variability, movements etc., and the bedside device 1 assesses the user's sleep cycle, based on this data. Preferably, the bedside device 1 may be configured to recognize a light sleep phase, a deep sleep phase, and an REM sleep (also called 'paradoxical' sleep) phase. In an embodiment, the bedside device 1 is configured to record the data over several nights and then obtains a personalised account of the user's sleep cycles and their manifestations.

In an alternative embodiment, the above described assessment of the user's sleep cycles is performed by the mobile terminal 7 (and/or by any additional or replacement device such as computer, laptop, tablet etc.), either alone or in combination with the bedside device 1. Notably, the mobile terminal 7 can be coupled directly to the sleep sensing unit 2.

The memory unit 141 may also store multiple adaptive sequences. The adaptive sequences are provided in form of light and sound programs, i.e. pre-defined or pre-set lights (colors, intensity, changes in colors and/or intensity of the lights) and sounds (music, relaxing sounds, and the like), which are played under specific circumstances. The adaptive sequences (light and sound programs) are designed to assist the user when falling asleep, awakening, remembering dreams etc. The light and sound programs are preferably performed based on the assessment of the user's sleep cycles and/or at predetermined time of the day. The light and sound programs will be described in greater detail below.

In one embodiment, the loudspeaker 4 and the light source 3 of the bedside device 1 are provided to play certain adaptive sequences (light and sound programs) in order to assist the user in falling asleep and/or waking up. The processing unit 140 is configured to decide which of the light and sound programs will be played. The decision may be based on one or more of the following: time (e.g. whether it is evening or morning; whether an alarm has been set; etc.), the sensory data from the sensing unit 2, the microphone 11, the light sensor 12, the temperature sensor 13, the additional sensor device 8, and any further optional sensor devices, the actual phase of the user's sleep cycle, and the like. The system is preferably also adapted to let the user choose (pre-set) the light and sound program s/he wishes to play (preferably via the interface 19). The system is preferably further adapted for the user to be able to adjust light intensity and sound volume at any time, including during replaying the pre-defined or pre-set light and sound programs As an example of operation of the sleep assist system, when the user is falling asleep, the loudspeaker 4 plays sounds designed to relax the user. Preferably, the sounds are of decreasing volume, i.e. a decrescendo. The sounds are further adapted to decrease the user's breathing frequency.

Further, the light source 3 outputs the light the color of which is set and the intensity of which is dimmed in a way for the user to fall asleep naturally. In such case, the red color of the light may be dominant. Red color is chosen in order to induce production of melatonin.

When the user is awakening, the sounds and lights are rather stimulating than relaxing, with increasing intensity, designed for the user to get in an easier way out of the deeper sleep stages; the color of the light may be predominantly blue in order to inhibit melatonin.

Generally, the light program (color, intensity) is preferably chosen in accordance with the correlation between the lighting and production of melatonin (the hormone responsible for the sleep-wake cycle). The sound program replicates the circadian rhythm's frequency and pattern. The adaptive sequences (light and sound programs) relax users while s/he is falling asleep, and stimulate him/her upon waking up.

Further, the bedside 1 device may asses—the user's sleep phases (such as deep sleep, REM, etc.) based on the sensory data (as specified above). To this end, the processing unit 140 and the memory unit 141 of the bedside device may be used. The processing unit 140 may be also configured to adjust the light and sound programs to be played based on the data obtained and the results deduced therefrom.

For example, the adaptive sequence played when the user is falling asleep may react on the actual user's state; if the user is falling asleep quicker/slower than expected, the adaptive sequence may be adjusted accordingly. Further examples are given below.

The user may pre-set his/her preferred time to be awakened. Subsequently, the sleep assist system determines when the user enters a light sleep phase, and awakens the user at the optimal moment. The awakening moment is based on the pre-set time and the sleep phase. For example, if the user wishes to be awakened not earlier than 6.30 and not later than 7 am; If at 6.30 the user is in deep sleep, nothing is done during 10 minutes. If the user is still in deep sleep at 6.40, then some short flash of light are played (to help the user to leave deep sleep, and the waking program starts. If at 6.30 the user is awake or in light sleep or in REM phase, the waking program starts (without light flashes).

The waking program is preferably a predetermined adaptive sequence (appropriate light and sound program). Preferably, the adaptive sequence is either pre-selected by the user, or is pre-set based on the user's sleep cycles and/or previous experience with that particular sequence. Examples of the selection of the light and sound programs based on the sleep phases are shown on FIGS. 3a, 3b and 3c. In these Figures, W denotes the user in a awake state; REM denotes the user being in REM phase (paradoxal sleep); L denotes the user being in light sleep; D denotes the user being in deep sleep.

Figure 3A:
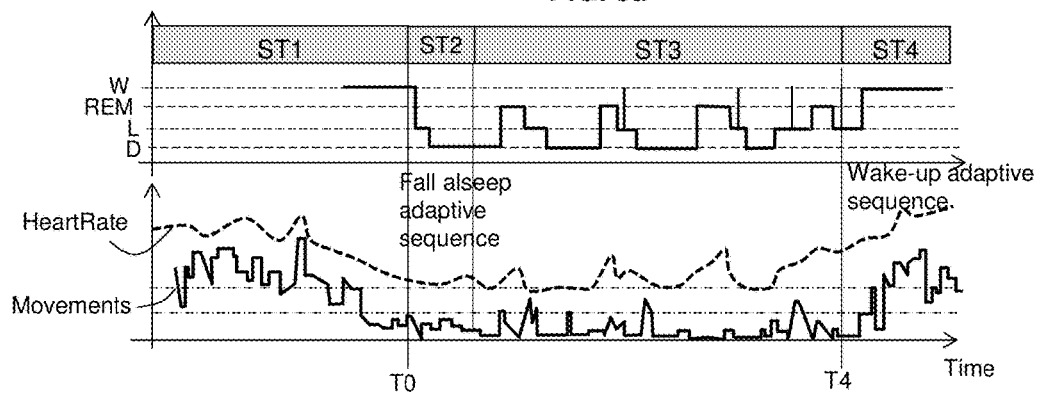
FIGS. 3a, 3b and 3c are time charts, illustrating light and sound programs assisting user's sleep

FIG. 3a shows an example of a normal sleep cycle. At the beginning of the phase ST1, the user is wide awake but begins to calm down; the heart rate begins to fall. The prevailing color of the light is preferably red, and the sounds are rather relaxing. At the end of phase ST1, at a certain time T0, the user is determined to have started to fall asleep. Adaptive sequence designed to assist the user to fall asleep is then played. Preferably, the fall asleep adaptive sequence is more relaxing, with lights dimmed and the sounds less loud. Preferably, the sounds and lights are 'disappearing'.

At the phase ST2, the user is continuing to falling asleep; the fall asleep light and sound program is continued to be played before the user is determined to have fallen asleep, i.e. entered phase ST3. Preferably, the system is configured to stop playing the light and sound program automatically once the user is detected to have fallen asleep.

During the night, the user is monitored. When it is determined that the user sleeps normally, no light and sound program is played. It should be noted that during the night, the user usually goes through several sleep cycles (i.e. succession of light sleep phase L, deep sleep phase D and REM sleep phase.

Once the user's heart rate and/or movements indicate that the user is in a light sleep L at T4 (beginning of phase ST4), and time to wake up approaches, the wake-up adaptive sequence is played, i.e. light (preferably blue lights) and sound program is provided to assist the user in awakening.

Figure 3B:
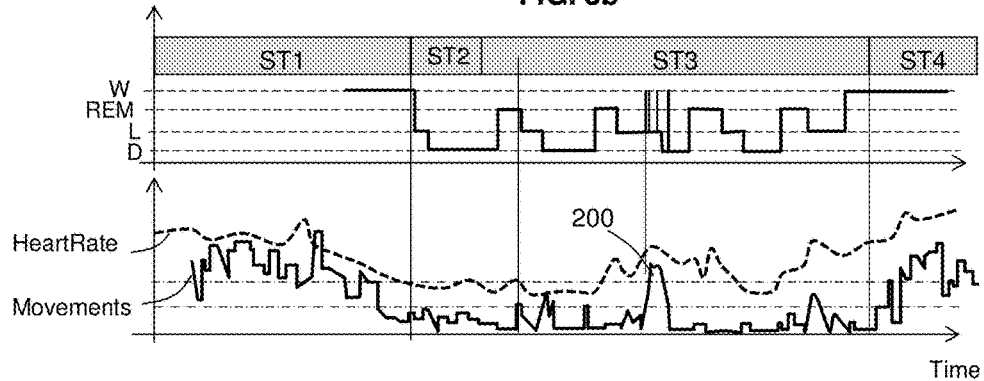

FIG. 3b shows an example of a night during which a distraction occurred. At the end of phase ST2, the user falls asleep. During the deep sleep phase D, a distraction 200 occurs; the user's heart-rate shows that the user is either close to be awakened, or completely awakened. In such situation, a light and sound program is played to assist the user in easily fall asleep again and enter the deep sleep phase as smoothly as possible.

Figure 3C:
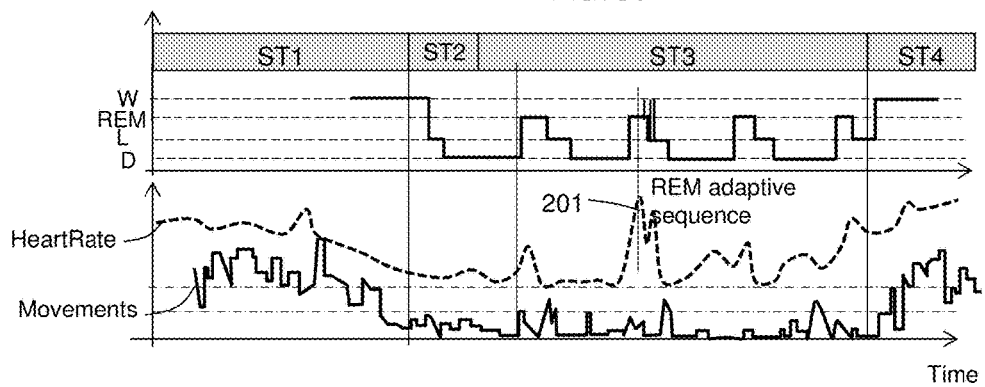

FIG. 3c shows an example of the situation, when the user is determined to have entered the REM sleep phase (paradoxal sleep). The heart rate and respiration rate variability increase 201 and absence of movement indicates that the REM phase has been entered; at that moment, REM light and sound program may be played. The REM light and sound program is designed to help the user to remember his/her dreams. The use of the REM light and sound program is preferably pre-set, i.e. prior to the night when the playing of this sequence occurs, the user selects that he wishes this sequence to be played during the night.

In one alternative embodiment, the sounds may be played by the mobile terminal 7. In one example, the lights are omitted entirely; in another example, the sounds are played by the mobile terminal 7, while the lights are played by the bedside device 1.

Figure 9:
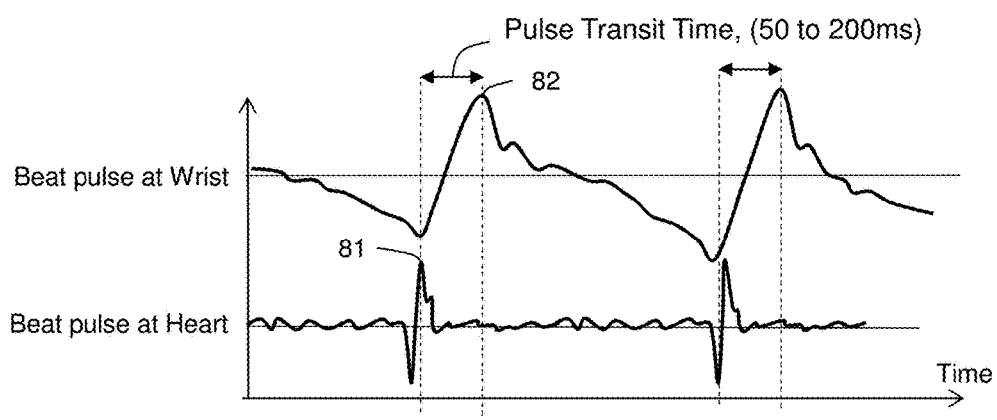
FIG. 9 illustrates an example of how to assess the stiffness of the arteries
Figure 5:
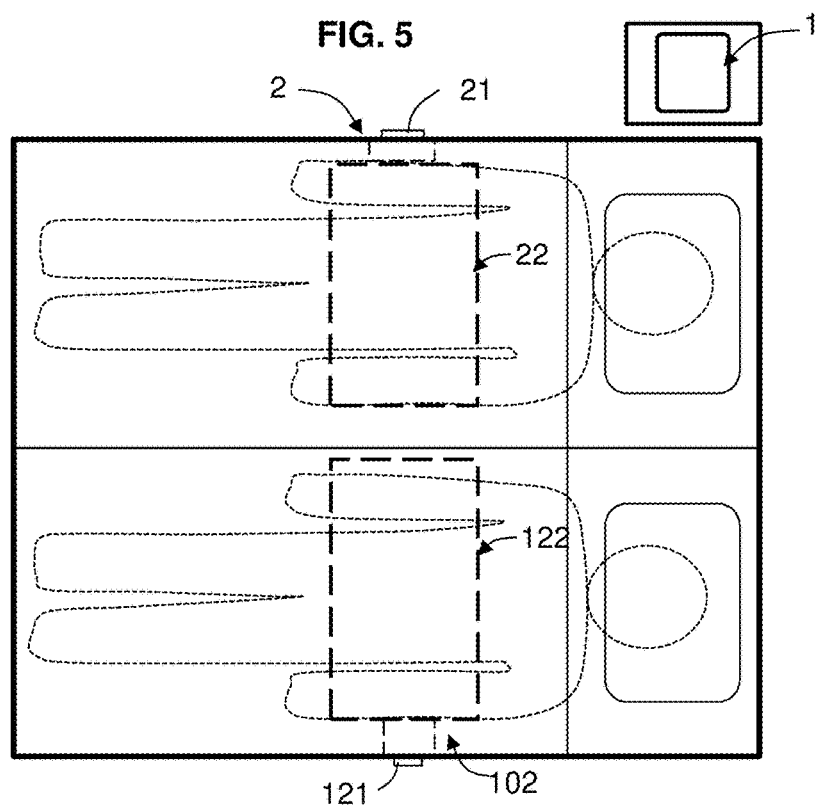
FIG. 5 shows a double bed equipped with the sleep sensing system
Figure 6:
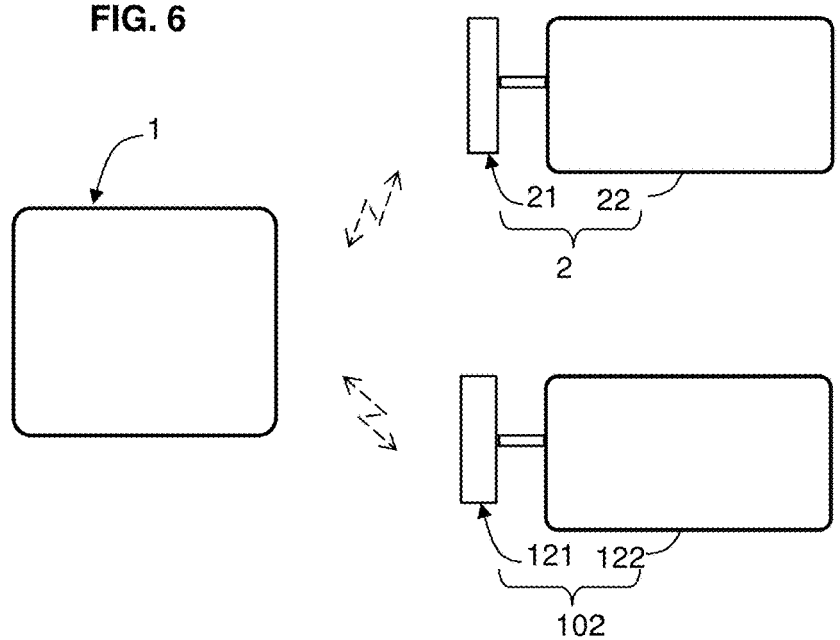
FIG. 6 is a schematic functional block diagram of the system of FIG. 5

Other examples of the operation of the sleep assist system are as follows:

a) The sensory data may be used to determine when and how many times during the night the user was awakened. This data may be correlated with the data recorded from the microphone 11, the light sensor 12, the temperature sensor 13 and/or the air quality sensor 16. The user may be later given the information on quality of his/her sleep, and what wakes him/her up.

b) The microphone 11 together with the sleep sensing unit 2 and optionally the additional sensor device 8 may be used to detect movements, sounds and other signs of stress (such as increased heart rate and decreased heart rate variability, quick and shallow breathing, etc.), and the bedside device 1 may subsequently provide a light and sound program adapted to relax the user. (See FIGS. 3a-3c for an example.)

c) The light source 3 is preferably adapted to provide reading light which is body-clock-optimized, i.e. its color and/or intensity is designed to minimize any unwanted body clock phase delay or phase advance. Preferably, the reading light is switched on easily through the user interface 19, preferably by a single gesture.

d) The light source 3 may output light of such color and intensity so as to help the user cope with jet-lag. By proper lighting, the user's body clock may be adjusted by creating body clock phase delay or body clock phase advance. The bedside device 1 may also be configured to offer a jet-lag prevention program, which helps the user to adjust his/her body clock to the time zone he is about to travel into.

e) The light source 3 and the loudspeaker 4 may create power nap adaptive sequence (light and sound program), designed for short nap (short relaxation) during the day. Preferably, the power nap adaptive sequence reacts to the sensory data in real-time, so as to further help the user get the most from even a short-time relaxation/nap.

f) The light source 3 and the loudspeaker 4 may create a snoring relieving adaptive sequence when the user is determined by the microphone 12 and/or other sensors to be snoring. The snoring relieving adaptive sequence may be designed for the snoring user, for his/her partner sleeping in the same room, or for both.

g) The microphone 11 together with the sleep sensing unit 2 may be used to monitor whether the user suffers from sleep apnea. If determined so, the user's state may be further monitored and assessed, or downloaded by an authorised medical person. More specifically, the microphone 11 may capture the sounds of the user snoring and breathing irregularly and/or with pauses. The bedside device 1 and/or the mobile terminal 7 then assesses whether the user stops breathing and therefore whether s/he suffers from sleep apnea. Alternatively, the sensing unit 2 may detect user breathing irregularly and/or with pauses through the changes in pressure on the sensing unit 2. The sensing unit 2 may be further adapted to measure vibrations caused by the user's snoring; the bedside device 1 and/or the mobile terminal 7 then correlates the pressure changes due to breathing and the vibrations caused by snoring to assess whether user suffers from the sleep apnea. As a further alternative, the additional sensor device 8 may be adapted to measure the drops in the blood oxygenation caused by the pauses in the user's breathing; the bedside device 1 and/or the mobile terminal 7 and/or the additional sensor device 8 then may assess whether the user suffers from sleep apnea. All the described detection methods may also be combined with each other, or all the methods may be combined together, to enhance the measurements.

h) The microphone 11 together with the sleep sensing unit 2 may be used to monitor whether a female user who is pregnant is about to give birth. If this is the case, early signs of labor can be identified and an authorised medical person may be alerted.

i) The microphone 11 together with the sleep sensing unit 2 and optionally the additional sensor device 8 may be used to detect the user's movements during the night, and more particularly, it may be used in assessment of the sleep movement disorders, such as periodic limb movement disorder, or the restless leg syndrome, or other such conditions.

j) The sensing unit 2 together with the additional sensor device 8 may be used for assessing the state of the user's blood vessels. The additional sensor device 8 may be adapted to detect the user's pulse on the user's wrist; the sensing portion 22 of the sensing unit may detect the user's heart rate directly from the changes of pressure exerted on the sensing portion 22. The data from the two sensors may be correlated. The time elapsed between the moment the heart moves and the moment the wrist shows a pulse may be calculated, and the stiffness of the user's arteries may be deduced. Illustration of the principle is shown in FIG. 9. The Pulse Transmit Time, i.e. the time between the pulse at heart, sensed by the sleep sensing unit 2, and the pulse at wrist, sensed by the additional sensor device 8, is assessed, and the stiffness of the arteries may be deduced; the time delay between the beat at heart 81 and the beat at wrist 82 is generally comprised between 50 ms and 200 ms. The assessment may be based on the measurements of the Pulse transit Time between the BCG signal measured by the first sensing unit 2 and the PPG signal measured by the additional sensor device 8. To this end, the additional sensor device 8 may be adapted to measure the user's heart pulse (e.g. PhotoPlethysmoGraphy sensor), the sensing unit 2 may be adapted to measure balistography signal, namely 'BCG', and the system is further configured to correlate this data and assess the stiffness of the user's arteries.

k) The sleep assist system may be configured to assess the heart volume stroke or at least its evolutions based on the measurements of the amplitude of the BCG signal measured by the sensing unit 2. If the system is used this way, the sensing unit 2 may be adapted to measure balistography signal.

l) The additional sensor device 8 may be further adapted to measure the user's heart pulse (e.g. PhotoPlethysmoGraphy sensor). The sensing unit 2 may be adapted to measure balistography signal. Based on this data, the system may assess the blood pressure or at least its evolutions based on the combination of the measurements of arterial stiffness, volume stroke and heart rate.

m) The sensing unit 2 may be used to measure and monitor the user's weight and its variations. In other words, the system is adapted to measure the variations of the user's weight over possibly long period of time. To do so, the period in the night where the largest pressures are seen during a sufficient time are averaged.

n) The sleep sensing system and its sensory data may be used by the elderly, the sick or disabled; in case of the unexpected problem (fit, seizure, attack), the system may provide an alert for relatives, carers and/or medical personnel.

o) For female users, the sleep assist system may provide information about the user's menstrual cycle. Once the sleep assist system determines the user has entered deep sleep, the sleep assist system measures heart rate of the user and assesses the phase of the cycle; the heart rate may be measured with data from the first sensing unit 2 and/or the additional sensor device 8, preferably correlation from both sources.

p) The pneumatic function of the sensing unit 2, if provided, may be used to increase user's comfort and/or to provide the user with light massage.

q) Further, the pneumatic function, if provided, may be used for babies to simulate the mother's heart beat through light pulses; the quality of the baby's sleep may thus be increased.

r) The bedside device 1 may be coupled to further devices. The sleep assist system may thus be supplemented by third-party services and data, to provide the user with even more comprehensive information. For example, environment sensors, body sensors etc. may be provided by third party, coupled either wirelessly or via a wire to the bedside device 1, and data thereof may be used to obtain information about user's sleep cycles, quality of sleep, health, etc. Further, the obtained data and/or information may be used in deciding and/or adapting the light and sound programs (adaptive sequences).

s) The sleep assist system, with all the data it provides, may offer to the user personalized insights and advices on how to improve sleep quality through adjustment of personal habits. This can for instance include personalized Cognitive Behavior Therapy programs.

t) When the user is awake but lying in the bed and getting ready to go to sleep, the sleep assist system may assess the level of stress (by measuring the heart rate and/or the user's movements). When the user is determined to be stressed, a light and sound program may be played to help relieve the stress and to relax the user. The time the sequence is being played may be based on the further measurements of the level of stress of the user during playing the sequence, i.e. the program is continued as long as the user is in tension, and once the user is determined to relax, the light and sound program is stopped. Alternatively, the user may himself decide to stop the program.

All the above described functions may be pre-set and stored in the bedside device 1. The user may be able to change or redefine the adaptive sequences (light and sound programs) in order to receive a program which suits him/her best. The bedside device 1 may also be programmed to adapt to the user's sleep cycles etc. based on the sensory data obtained.

The sensory data recorded from the sensing unit 2, the microphone 11, the light sensor 12, the temperature sensor 13, the air quality sensor 16 and/or the additional sensor device 8 are stored in the memory unit 141 of the bedside device 1. Upon the request of the user, the data may be transmitted via the communication interface 15 of the bedside device 1. The data may be transmitted for example to the mobile terminal 7. Alternatively, the data may be sent to the mobile terminal 7 regularly, for example once or twice a day, in a pre-set time. Alternatively, the data may be sent to computer, laptop, tablet or other such device which replaces and/or supplements the mobile terminal 7.

To this aim, the mobile terminal 7 may be equipped with specialized application (a specialized software), which is configured to transmit such request for data transmission to the bedside device 1. Alternatively, the transmission may be effected automatically, for example in a specified time, specified part of the day, after a specified event occurred, etc.

The mobile terminal 7 is further adapted to store the data received from the bedside device 1 and/or the sensors in its own memory, and process it. Preferably, all the obtained data are correlated. The specialized application, provided in the mobile terminal 7, is then adapted to provide the user with various information relating to his/her health, heart rate, breathing frequency, quality of sleep, sleep cycles, number of awakenings during the night, correlation between the awakenings and the sensory data obtained by the bedside device 1 and/or the additional sensor device 8, and the like. The user may then use the application and/or information obtained therefrom to assess his/her physical state, plan exercise, adjust his/her environment during the night, etc.

The application, provided in the mobile terminal 7, may be adapted to:
- display various information about the user's sleep, e.g. graphs of sleep quality, sleep stage, sleep hypnogram and the like
- receive feedback from the user on past night sleep quality; to this aim, the application may for example display questions on the user's feelings, receive responses, and evaluate the responses
- drive the bedside device 1 to run the adaptive sequences (light and sound programs), either manually launched by the user or triggered at a specified time (for example a morning wake-up program)
- run the adaptive sequences (light and sound programs) itself, either manually launched by the user or triggered at a specified time (for example a morning wake-up program)
- record and store data received from the bedside device 1, data received from the sensing unit 2 and possible further sensors, optionally record and store data received from the sensors of the mobile terminal 7 (if the mobile terminal is provided with such sensors) and optionally record and store data from third party services and sensors,
- communicate in real-time and/or in batch the recorded data (movements, heart rate, breathing rate, sleep cycles etc.) to the bedside device 1, the sensing unit 2 and/or any additional computer, laptop, tablet or the like which the user uses along with the mobile terminal 7,
- adapt light and sound programs and time-triggered events (like a wake-up program) based on the data received from the bedside device 1, the user feedback and/or any third-party data.

The bedside device 1 is preferably programmable. The user is provided with a user interface, through which the user may input his/her instructions. The user interface may be integrated in the bedside device 1, as described above. The user interface may be also provided by the application provided in the mobile terminal 7. The specialized application comprised in the mobile terminal 7 preferably provides options for controlling the bedside device 1, such as setting the alarm time, choosing preferred light and sound programs for awakening and falling asleep, and the like. The mobile terminal 7 also enables the user to review his/her data from the bedside device 1, and obtain feedback from the bedside device 1. In an embodiment, the bedside device 1 itself may be provided with a simplified user interface, while full user interface is provided by the mobile terminal 7, as described above.

In an alternative embodiment, the mobile terminal 7 is also adapted to transmit to the bedside device 1 data which may serve to determine and/or select the right light and sound programs, such as the history of user's reaction to specific light and sound programs, the feedback provided directly by the user, etc.

In case the additional sensor device 8 is provided (see FIG. 4 for schematic views of such system), the additional sensor device 8 may transmit the sensory data obtained thereby to the bedside device 1. The data are subsequently collected by the mobile terminal 7. Alternatively, the data may be transmitted directly to the mobile terminal 7. Preferably, the additional sensor device 8 is programmable, and the mobile terminal 7 provides interface for programming the additional sensor device 8.

The additional sensor device 8 may comprise one or several additional sensors, used to assess the user's skin temperature, heart rate, etc. The additional sensor device 8 may be further adapted to measure the parameters related to the physical activity, such as distance run by the user, the number of steps taken, the calories burned etc.

All the data obtained by the additional sensor device 8 may be stored in the memory, provided for that purpose in the additional sensor device 8. The data may be subsequently transmitted, preferably wirelessly, to the bedside device 1 and/or the mobile terminal 7. The data are subsequently processed by the respective device. The data obtained by the additional sensor device 8 may be then correlated with the data obtained by other means (such as the sensing unit 2, the microphone 11, the light sensor 12, the temperature sensor 13, the air quality sensor 16 etc.). An improved overall image of the user's physical state (fitness, health) may be thus obtained. The effects of physical activity of the quality of the user's sleep may be assessed. Consequently, the sleep assist system may provide the user with improved personalised assistance in his/her sleep as well as with general lifestyle advices (such as exercise—timing and intensity).

Further, a scale 9 (for example, a so-called smart-scale) may be also part of the system. The scale may be coupled to the mobile terminal 7 and/or the bedside device 1 to provide more accurate information about the user's weight, bodily fat etc. The data obtained by the scale 9 may be correlated with the above described data and provide further precision to the information.

The sleep assist system may be provided for a single user, i.e. on a single bed. The sleep assist system may be also provided for two users (for example a husband and a wife) sleeping on a double bed (see FIGS. 5 and 6). In the latter case, there may be a single bedside device 1, connected to two different sensing units 2, 102. In case of the double bed, the sleep assist system functions substantially in the same way as the system provided for a single user/single bed.

In case of double bed, each user has his own sensing unit 2, 102, which collects his or her data. The bedside device 1 may be thus configured to process two distinct data sets obtained from two distinct sensing units 2, 102. In case the sleep assist system uses also the additional sensor device 8, the bedside device 1 may be further configured to obtain and process data from two different additional sensor devices (or two sets of additional sensor devices, if the users use more than one additional sensor device each).

Each of the sensing units 2, 102 is provided with its own electronic unit 21, 121, and with its own sensing portion 22, 122. Each of the electronic units is further provided with its own communication interface, in order to be able to connect to and communicate with the bedside device 1.

Similarly, the system may be provided with at least two mobile terminals (at least one for each user), at least two additional sensor devices (at least one for each user), etc.

The sleep assist system provided for the double bed may be adapted to perform some or all of the above described functions.

Moreover, the bedside device 1 of the sleep assist system for double bed may be adapted to take into account both users and their sleep cycles in determining e.g. the optimal moment for the users to be awakened. For example, when the first user is already in the light sleep, but the second user is still in the deep sleep phase, the alarm may be postponed until the second user also enters the light sleep phase. Both of the users may then be awakened simultaneously, in an optimised moment for both. Further, the adaptive sequences (light and sound programs) played may be set according to the wishes and/or sleep cycles of both users.

In case of two users using the sleep assist system, the data from each sensing unit 2, 102, as well as from the bedside device 1, may be correlated. The result obtained may help to assess the influences of each user on his/her partner. For example, if the husband snores and the wife is awakened several times during the night, it may be established whether the wife is awakened by the husband's snores or by other disturbances, such as cars passing by and casting light onto the wife. Further, when one of the users creates other disturbances during the night (such as teeth grinding, excessive or periodic movements of the limbs etc.), the bedside device 1 and/or the mobile terminal 7 correlate these disturbance with quality of sleep of both users and the users are then informed.

Once data is collected from the sensing units 2, 102, it is transmitted to the bedside device 1 and/or to the mobile terminal 7. The bedside device 1 and/or the mobile terminal 7 are preferably adapted to evaluate the data and assess whether the detected movements really occurred or whether the detected movements of the first user is just an echo of the movements of the second user.

This is illustrated on FIG. 7. The first signals 23 coming from the first sensing unit 2 outputs that at certain moments 108, the first user moved. At the same moment, a very similar data with second peaks 118 in substantially the same moments as the first peaks 108 is obtained from the second signals 123 coming from the second sensing unit 102. However, the intensity of the movements recorded by second sensing unit 102 is lower than the intensity recorded by first sensing unit 2 (the amplitude of second peaks 118 is lower than that of first peaks 108). The bedside device 1 and/or the mobile terminal 7 may identify that the second peaks 118 recorded by the second sensing unit 102 is an echo of the first peaks 108 generated by the first user, and not an actual movement of the second user. The first peaks 108 are thus attributed to the movements of the first user, but the second peaks 118 are not attributed to the movements of the second user, but are interpreted as an echo of the movements of the first user instead. Conversely, when the second user actuals moves 119, it produces an echo on the first sensing unit, but the control unit eliminate this isde effect signal through correlation.

FIG. 8 illustrates an alternative embodiment, where the double bed is provided with only one sensing unit 2. In such case, the sensing unit 2 is positioned at least under the chest area of both of the users; it is adapted to perform all the functions described above for the single bed system. Further, the double bed system in such case may be supplemented by additional sensor devices 8, 128 provided for both users. The users may wear individually the additional sensor devices 8, 128 for example on their wrists. The additional sensor devices 8, 128 may measure the users' heart rates, skin temperature etc., and provide the common bedside device 1 with two distinct data sets. The data obtained from the additional sensor devices 8, 128 may then complement the data obtained by the sensing unit 2; the data sets are correlated and the information about the users' sleep cycles, quality of sleep, the relation between distractions such as noises and lights during the night and the quality of sleep, and the like.

Figure 10:
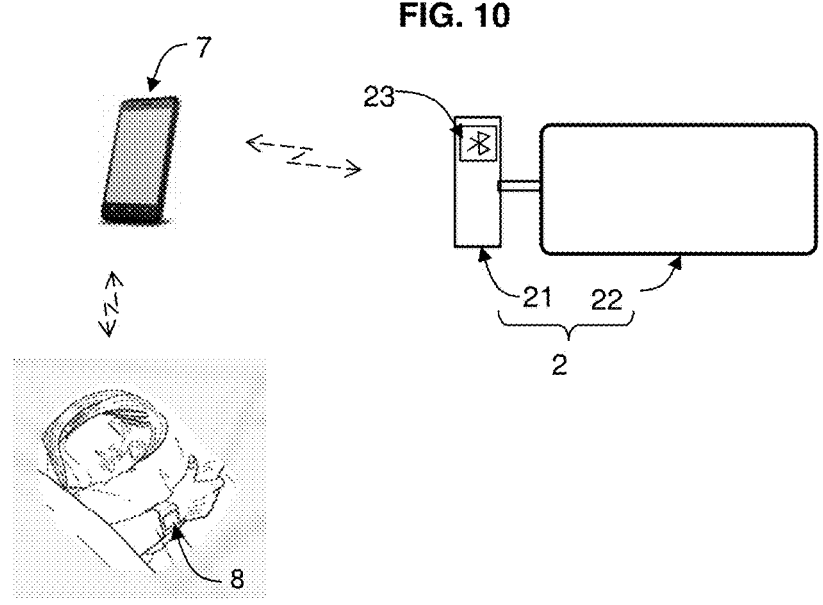
FIG. 10 shows an alternative embodiment of the invention.

In an alternative embodiment (see FIG. 10) of the present invention, some or all of the functions of the bedside device 1 may be taken over by the mobile terminal 7. If the functions are completely taken over by the mobile terminal, the bedside device 1 may be omitted.

For example, for female users, the first sensing unit 2 and/or the additional sensor device 8 may provide information about the user's menstrual cycle. Once the sensing unit 2 and/or the additional sensor device 8 determines that the user has entered deep sleep, the sensing unit 2 and/or the additional sensor device 8 measure heart rate of the user and assesses the phase of the cycle. The obtained information is transmitted directly to the mobile terminal 7, where the user may visualise it and possibly further process the information. The mobile terminal 7 may be used to correlate the information thus obtained with information on other aspects of user's state (such as sleep phase/cycle assessment, number of awakenings during the night, exercise/work out activities etc.

As a further example, the sensing unit 2 together with the additional sensor device 8 may be used for assessing the state of the user's blood vessels. The additional sensor device 8 may be adapted to detect the user's pulse on the user's wrist; the sensing portion 22 of the sensing unit may detect the user's heart rate directly from the changes of pressure exerted on the sensing portion 22. The data from the two sensors may be correlated. The time elapsed between the moment the heart moves and the moment the wrist shows a pulse may be calculated, and the rigidity of the user's arteries may be deduced. The information may be again displayed and processed directly by the mobile terminal 7, similar to the processing of other information described above. Illustration of the principle is shown in FIG. 9. The Pulse Transmit Time, i.e. the time between the pulse at heart (ref 81), sensed by the sleep sensing unit 2, and the pulse at wrist (ref 82) sensed by the additional sensor device 8, is assessed, and the stiffness of the arteries may be deduced.

The assessment may be based on the measurements of the Pulse transit Time between the BCG signal measured by the sensing unit 2 and the PPG signal measured by the additional sensor device 8. To this end, the additional sensor device 8 is adapted to measure the user's heart pulse (e.g. PhotoPlethysmoGraphy sensor), the sensing unit 2 is adapted to measure balistography signal, and the mobile terminal 7 may be further configured to correlate this data and assess the stiffness of the user's arteries.

The system may also be configured to assess the heart volume stroke or at least its evolutions based on the measurements of the amplitude of the BCG signal measured by the sensing unit 2. If the system is used this way, the sensing unit 2 may be adapted to measure balistography signal. The mobile terminal 7 processes the data.

Further, the additional sensor device 8 may be further adapted to measure the user's heart pulse (e.g. PhotoPlethysmoGraphy sensor). The sensing unit 2 may be adapted to measure balistography signal. Based on this data, the mobile terminal 7 may assess the blood pressure or at least its evolutions based on the combination of the measurements of arterial stiffness, volume stroke and heart rate.

In a further example, when the system is used to measure user's weight and its changes over a period of time, the bedside device 1 may be replaced by the mobile terminal 7.

The invention claimed is:

1. A system to monitor a user's sleep and to assess various physiological parameters of the user, the system comprising:
   a bedside device comprising at least a processing unit and a memory unit having non-transitory computer executable instructions, the bedside device further comprising at least one of the following: a loudspeaker, a light source, a microphone, a light sensor, a temperature sensor, a humidity sensor, a control unit, an air quality sensor, a display unit, and a user interface;
   a first sensing unit adapted to be positioned in the user's bed, the first sensing unit comprising one or more sensors adapted to sense at least pressure and/or changes in pressure exerted by the user lying in the bed, the first sensing unit comprising an air bladder the first sensing unit being adapted to measure ballistocardiography signals,
   an additional sensor device, configured to be in contact with the user's body, such that the additional sensor device is worn by the user on the user's wrist, having a photoplethysmography sensor and configured to measure at least heart pulses of the user,
   wherein the first sensing unit is coupled to the bedside device, wherein the additional sensor device is coupled to the bedside device, the processing unit is configured to correlate the data obtained from both the first sensing unit and the additional sensor device, and to deduce therefrom cardiovascular parameters including at least user's heart rate, user's heart rate variability and user's breathing frequency,
   wherein the processing unit is further configured to determine a first instant sensed by ballistocardiography of the first sensing unit, said first instant being representative of the user's heart ventricular contraction, to determine a second instant of an arrival of a corresponding pulse at the user's wrist, sensed by photoplethysmography of the additional sensor device, and to measure a pulse transit time defined as the time difference between first and second instants, and
   wherein the processing unit is further configured to assess the stiffness of the user's arteries based on the measurements of pulse transit time.

2. The system as in claim 1, wherein the bedside device further comprises a wherein the processing unit is further configured to:
   monitor the user's sleep, assess the user's sleep cycles and the phase of sleep cycle, by using data collected from the first sensing unit and the additional sensor device, and
   provide the user with at least one light and sound program via the bedside device, the light and sound program being based on the assessment of the user's sleep cycles and the phase of sleep cycle.

3. The system as in claim 1, wherein the processing unit is configured further configured to assess heart volume stroke and/or its evolutions based on the amplitude of the signal measured by the first sensing unit, and from the pulse transit time.

4. The system as in claim 3, wherein the processing unit is further configured to assess blood pressure or at least its evolutions based on the combination of arterial stiffness, heart volume stroke and heart rate.

5. The system as in claim 1, the bedside device further comprising a microphone, wherein the processing unit is further configured to determine when a user suffers from sleep apnea based on a pause in breathing cycle sensed via the first sensing unit and a blood oxygenation drop sensed via the additional sensor.

6. The system as in claim 1, wherein the system further comprising a mobile terminal, the mobile terminal being configured to receive and to display the information obtained by the bedside unit, the sensing unit and/or the additional sensor device, wherein the mobile terminal is further configured to receive feedback from the user.

7. A system to monitor a user's sleep, and to assess various physiological parameters of the user, the system comprising:
   a mobile terminal comprising at least a control unit and a display,
   a first sensing unit adapted to be positioned in the user's bed, the first sensing unit comprising one or more sensors adapted to sense at least pressure and/or changes in pressure exerted by the user lying in the bed, the first sensing unit comprising an air bladder, the first sensing unit being adapted to measure ballistocardiography signals, an additional sensor device, configured to be in contact with the user's body, such that the additional sensor device is worn by the user on the user's wrist, having a photopléthysmography sensor and configured to measure at least heart pulses of the user, wherein the first sensing unit is coupled to the mobile terminal, wherein the additional sensor device coupled to the mobile terminal, the mobile unit is configured to correlate the data obtained from both the first sensing unit and the additional sensor device, and to deduce therefrom cardiovascular parameters including at least user's heart rate, user's heart rate variability and user's breathing frequency wherein the mobile unit is further configured to determine a first instant sensed by ballistocardiography of the first sensing unit, said first instant being representative of the user's heart ventricular contraction, to determine a second instant of an arrival of a corresponding pulse at the user's wrist, sensed by photopléthysmography of the additional sensor device, and to measure a pulse transit time defined as the time difference between first and second instants, and wherein the mobile is further configured to assess the stiffness of the user's arteries based on the measurements of pulse transit time.

8. The system as in claim 7, wherein the mobile unit is further configured to assess heart volume stroke and/or its evolutions based on the amplitude of the signal measured by the first sensing unit, and from the pulse transit time.

9. The system as in claim 7, wherein the mobile unit is further configured to assess blood pressure or at least its evolutions based on the combination arterial stiffness, heart volume stroke and heart rate.

10. The system as in claim 7, wherein the bedside device further comprising a microphone, and wherein the mobile unit is further configured to determine when a user suffers from sleep apnea based on a pause in breathing cycle sensed via the first sensing unit and a blood oxygenation drop sensed via the additional sensor.

* * * * *